US00PP17080P2

(12) United States Plant Patent
Lemon

(10) Patent No.: US PP17,080 P2
(45) Date of Patent: Sep. 5, 2006

(54) ***GERANIUM* PLANT NAMED 'MAESTRO SALMON'**

(50) Latin Name: *Pelargonium×hortorum*
Varietal Denomination: Maestro Salmon

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,055

(22) Filed: Jul. 8, 2005

(51) Int. Cl.
*A01H 5/00* (2006.01)

(52) U.S. Cl. ..... Plt./327

(58) Field of Classification Search ..... Plt./327
See application file for complete search history.

*Primary Examiner*—Kent Bell
(74) *Attorney, Agent, or Firm*—The Webb Law Firm

(57) ABSTRACT

'Maestro Salmon' is a new variety of *geranium* having dark leaves, free flowering, and pale salmon colored flowers.

1 Drawing Sheet

Botanical classification: *Pelargonium×hortorum.*
Varietal denomination: 'Maestro Salmon'.

BACKGROUND OF THE INVENTION

The present invention comprises a new and distinct cultivar of *Pelargonium×hortorum* known by the varietal name 'Maestro Salmon'. The new variety was discovered in Lompoc, Calif. The new variety is a result of cross breeding Seedling #1509 (female parent) (unpatented) and 'Americana Light Salmon' (male parent) (U.S. Plant Pat. No. 7,936). The purpose of the breeding program was to introduce a compact and dark-leaved zonal *geranium*. The new variety has a paler flower color than its female parent. The new variety exhibits similar flower color to its male parent, but has a more compact habit. 'Maestro Salmon' is also more free flowering with a compact habit and exhibits excellent greenhouse and outdoor performance when compared to other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. using full light, 16° C. night temperature and 20° C. day temperature and grown in a soilless media with constant fertilizer at 200–250 ppm nitrogen and potassium. The new variety exhibits developed roots at 21 days at an average temperature of 23° C. and has a response time of six to seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
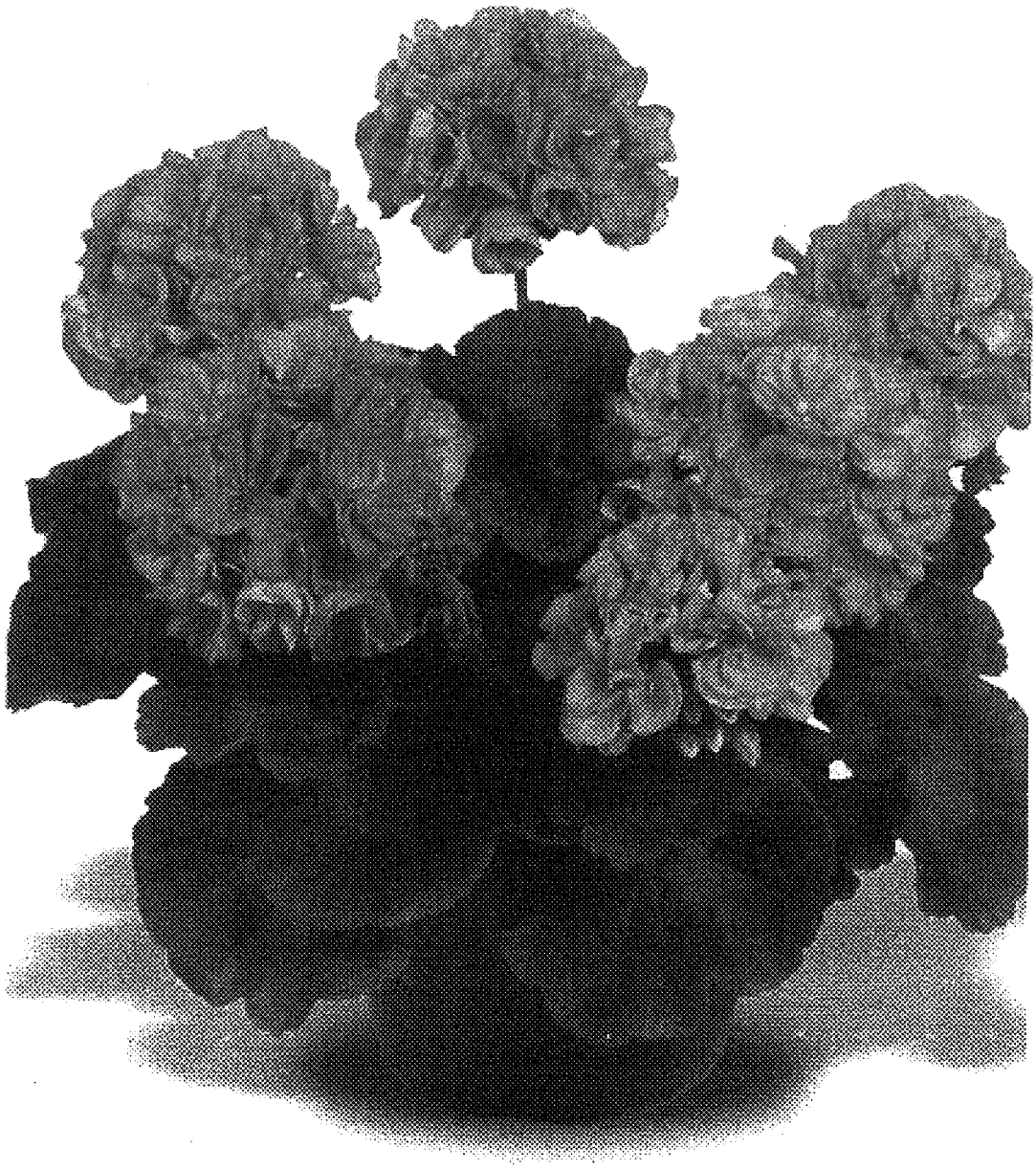

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S. Colour Chart of The Royal Horticultural Society of London.

PLANT

Market class: Zonal.
Time to initiate roots (days, temperature): About 7–10 days at about 23° C.
Time to develop roots (days, temperature): About 21 days at about 23° C.
Time to produce a finished flowering plant from a rooted cutting: About 6–7 weeks in a 10 cm. container.
Rooting habit: Good, normal.
Form: Round-mounded.
Height from media surface to top of foliage: 13.0–14.9 cm.
Height from media surface to top of flowers: 21.5–24.5 cm.
Plant diameter: 25.0–26.0 cm.
Strength: No artificial support is needed.
Branching habit: Free branching.
Stem:
- *Main stem length.*—10.3–10.7 cm.
- *Diameter.*—0.7–0.8 cm.
- *Color.*—Yellow-Green Group 144A.
- *Texture.*—Leathery texture.
- *Pubescence.*—Present.
- *Internode length.*—3–3.5 cm.

Lateral branches:
- *Length.*—Primary: 10.7–11.5 cm. Secondary: Plant is too young to measure.
- *Diameter.*—Primary: 0.6–0.7 cm. Secondary: Plant is too young to measure.
- *Internode length.*—2.3–3.5 cm.
- *Texture.*—Leathery.
- *Pubescence.*—Present.
- *Color.*—Yellow-Green Group 144A.

Foliage:
- *Arrangement.*—Alternate; opposite.
- *Stipules.*—Size: 1.2 cm. high by 0.8 cm. wide. Color: Yellow-Green Group 144A.

*Zone.*—Location: Faint zone from outer edge of leaf to ½ of the way toward the center. Color: Green Group 137B.
*Size of leaf.*—Length: 5.2–7.3 cm. Width: 6.2–9.0 cm.
*Shape of leaf* (*generally*).—Reniform with a stalked base.
*Shape of apex.*—Rounded in accordance with reniform leaf shape.
*Shape of base.*—Cordate.
*Texture.*—Velvety.
*Aspect.*—Leaves have a very slight slope increasing from point of connection toward the margin.
*Margin type.*—Crenate.
*Pubescence.*—Upper surface: Moderate. Lower surface: Moderate.
*Color.*—Young leaves: Upper surface: Green Group 137B. Lower surface: Green Group 138B. Mature leaves: Upper surface: Green Group 137A. Lower surface: Green Group 137B.
*Petiole.*—Length: 5.1–7.1 cm. Diameter: 2.0–2.5 mm. Color: Yellow-Green Group 144A.
*Veins.*—Venation type: Palmate. Color: Upper surface: Green Group 138A. Lower surface: Yellow-Green Group 145A.

INFLORESCENCE

Bud:
*Stage of development when bud characteristics determined.*—Bud shows color at side but sepals are not parting at the tips.
*Shape of cluster.*—Elliptical.
*Diameter of cluster.*—2.0–2.9 cm.
*Number of buds per cluster.*—9–16.
*Shape of individual bud.*—Ellipse.
*Length of individual bud.*—0.8–0.9 cm.
*Width of individual bud.*—0.5–0.6 cm.
Natural flowering season at specified location(s): Year round horticultural greenhouse crop.
Blooming habit: Continuous and free flowering.
Umbel diameter: 8.3–9.5 cm.
Umbel depth: 5.5–6.1 cm.
Borne: Umbel, flowers on pedicel, pedicel on peduncle.
Inflorescence position: Above foliage.
Number of inflorescences per lateral branch: 1–2.
Lastingness of an individual flower: 10–14 days.
Florets:
*Form.*—Flat and slightly cupped. As flowers mature, the florets gradually become more open/flat.
*Number per umbel.*—11–23.
*Diameter.*—3.8–4.5 cm.
*Depth.*—1.8–2.2 cm.
Petals:
*Color.*—The top two petals of the floret have a lighter coloration than the bottom petals.
*Upper surface.*—The top two or three petals are Red Group 56C with Red Group 48D speckling and venation, which is more pronounced towards the margin. The bottom third has a Red Group 48C band with Red Group 43C stripes on the far ends of the band. As these two stripes approach each other at the base of the petal, they form a "V". The point of connection then immediately fades to a White Group 155D. The bottom petals are Red Group 56C and have heavy Red Group 41C streaking, specks, and venation. On the bottom ⅓ of the petal there is a pronounced Red Group 41C "V" or "W". The point of connection then immediately fades to a White Group 155D.
*Lower surface.*—All petals are Red Group 56C with light Red Group 48C speckling and venation. The deepest color is a fine line on the margin. The connection point is White Group 155D. The top two or three petals have a more pronounced coloring on the bottom ⅓ margin as compared to the bottom petals.
*Shape.*—Inverted teardrop.
*Length.*—2.1–2.5 cm.
*Width.*—1.6–2.3 cm.
*Apex shape.*—Smooth and rounded.
*Base shape.*—Tapered to a point.
*Margin.*—Entire; smooth.
*Number per floret.*—6–13.
*Texture.*—Smooth.
*Tonality from a distance.*—Rich salmon orange flowers atop mounding medium-dark green foliage.
Petaloids:
*Quantity.*—0–2 per floret.
*Shape.*—Splits in a two-pronged unit or are tubular.
*Color* (*Upper and lower surface*).—Tubular petals have an inner and outer surface of Red Group 38C and fade to White Group 155D near the point where it connects to the pedicel. Split florets have an upper surface Red Group 38A and fade to White Group 155D at connection point. The undersides are Red Group 36C and fade to White Group 155D.
*Length.*—1.1–1.5 cm.
*Width.*—0.2–0.6 cm.
Pedicel:
*Length.*—2.1–2.6 cm.
*Diameter.*—0.13–0.15 mm.
*Color.*—Greyed-Purple Group 185A where the pedicel connects to the floret and fades to Yellow-Green Group 144A as the pedicel approaches the point where it connects to the peduncle.
Peduncle:
*Length.*—10.1–11.5 cm.
*Diameter.*—0.25–0.3 cm.
*Texture.*—A slightly rough leather texture with a slight to moderate amount of pubescence.
*Color.*—Yellow-Green Group 144A.
Sepal:
*Number.*—5.
*Pubescence.*—Moderate.
*Shape.*—Lanceolate.
*Width.*—0.2–0.4 cm.
*Length.*—0.8–1.0 cm.
Fragrance: No unusual fragrance.
Disease resistance: None observed.
Temperature tolerance: None observed.
Drought tolerance: None observed.

REPRODUCTIVE ORGANS

Stamens:
*Number* (*per flower*).—8–13.
*Filament.*—Length: 0.3–0.7 cm. Color: White Group 155D with the tip being Red-Purple Group 66A.
*Anthers.*—Shape: Oval-like with a slight curve. Length: 0.15–0.2 cm. Color: Grey-Purple Group 184A.

*Pollen.*—Color: Greyed-Orange Group 171A. Amount: Plentiful.

Pistils:

*Number.*—1.

*Length.*—0.7 cm.

*Style.*—Length: 0.2 cm. Color: Red Group 45C.

*Stigma.*—Shape: Style splits and radiates into 5 parts. Color: Red Group 45C. Size: 0.1 cm. high.

*Ovaries.*—Position: Superior. Pubescence: Present. Length: 0.4 cm. Width: 0.17–0.2 cm. Color: Yellow-Green Group 144B.

I claim:

1. A new and distinct variety of *geranium* plant named 'Maestro Salmon' as described and illustrated.

* * * * *